(12) United States Patent
Chang et al.

(10) Patent No.: US 11,771,729 B2
(45) Date of Patent: Oct. 3, 2023

(54) MACA EXTRACT AND USE THEREOF

(71) Applicant: KAOHSIUNG MEDICAL UNIVERSITY, Kaohsiung (TW)

(72) Inventors: Fang-Rong Chang, Kaohsiung (TW); Chin-Chung Wu, Kaohsiung (TW); Bing-Hung Chen, Kaohsiung (TW); Tsong-Long Hwang, New Taipei (TW); Shih-Wei Wang, Taipei (TW); Kartiko Arif Purnomo, East Java (ID); Yi-Hong Tsai, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 17/828,230

(22) Filed: May 31, 2022

(65) Prior Publication Data

US 2022/0387536 A1 Dec. 8, 2022

Related U.S. Application Data

(60) Provisional application No. 63/195,150, filed on May 31, 2021.

(51) Int. Cl.
*A61K 36/31* (2006.01)

(52) U.S. Cl.
CPC ........ *A61K 36/31* (2013.01); *A61K 2236/333* (2013.01); *A61K 2236/53* (2013.01); *A61K 2236/55* (2013.01)

(58) Field of Classification Search
None
See application file for complete search history.

*Primary Examiner* — Russell G Fiebig

(57) ABSTRACT

The present invention relates to a maca extract and uses thereof. The part of the maca extract extracted with polar solvent has anti-thrombotic activity, the part of the maca extract extracted with medium and low polarity solvents has anti-neutrophilic inflammatory and anti-allergic activities, the part of the maca extract extracted with low polarity solvent has anti-neutrophilic inflammatory activity and has pro-angiogenic activity.

3 Claims, 4 Drawing Sheets
(1 of 4 Drawing Sheet(s) Filed in Color)

MACA EXTRACT AND USE THEREOF

CROSS REFERENCE TO RELATED APPLICATION

The present application claims the benefit from U.S. Provisional application No. 63/195,150 filed on May 31, 2021, the contents of which are incorporated herein by reference in their entirety.

BACKGROUND OF THE INVENTION

1. Field of the Invention

The present invention relates to a maca extract and a use thereof, and more particularly, to a maca extract extracted using a specific solvent for anti-thrombotic, anti-neutrophilic inflammation, anti-allergic and pro-angiogenic purposes.

2. Description of the Related Art

Maca has a scientific name of *Lepidium meyenii* Walp., also called Peruvian ginseng, and belongs to the cruciferous plants serving as a medicinal plant in the Peruvian Andes. The tuber parts are used by local Peruvians as functional food and folk medicine for improving sexual function and fertility.

According to various pharmacological studies recently, the maca extract has various activities, such as anti-fatigue, nourishing tonic, anti-osteoporosis, anti-inflammatory, anti-viral, and anti-tumor activities.

In addition, according to the studies, the maca extract has an immune regulation function and a hepatoprotective activity, and is also effective in treating postmenopausal syndrome and benign prostate hyperplasia.

The tuber, which is the edible part of maca, contains a large amount of primary metabolites, such as carbohydrates, proteins and lipids, and various secondary metabolites such as alkaloids, flavonolignans, triterpenoids, and glucosinolates.

The alkaloid derivatives are known as biologically active ingredients, represents most of the secondary metabolites of maca that have been studied, and includes alkaloid amides (macamides), hydantoin derivatives (e.g., macahydantoins, meyeniihydantoins, macathiohydantoins, etc.), hexahydroimidazolethiazole derivatives (e.g., meyeniins), imidazole alkaloids (e.g., lepidiline), pyridine derivatives (e.g., macaridines) and pyrazole derivatives (e.g., macapyrrolins).

Over the past 30 years, maca has already been a sought-after natural health care ingredient as well as a dietary supplement, and has a high market value in various products around the world. Accordingly, a number of relevant scholars have conducted extensive research and exploration of maca so as to find ingredients and experimental evidences beneficial to the human body.

Maca is being spotlighted as a research subject in the natural health care product market, however, maca has further undiscovered phytochemical and biological activities.

SUMMARY OF THE INVENTION

In order to solve the above problem, the inventor(s) of the present invention performed extraction and separation through different solvents, and performed experiments on various extraction ingredients, thereby finding out active compounds and biological activities that people have not yet discovered from maca.

A maca tuber was extracted with an aqueous ethanol solution and then concentrated under reduced pressure to obtain a maca crude extract, and the crude maca extract was phase-separated and extracted using ethyl acetate and water, thereby obtaining an ethyl acetate layer and a first aqueous layer; thereafter, the first aqueous layer was phase-separated and extracted using an aqueous n-butanol solution to obtain a second aqueous layer and an n-butanol layer; and then, the ethyl acetate layer was phase-separated and extracted using a mixed solution of methanol and n-hexane, thereby obtaining a methanol layer and an n-hexane layer.

Next, the n-hexane layer and the methanol layer were eluted and purified using column chromatography to obtain 8 kinds of maca extract alkaloid derivative compounds as shown in FIG. 1; wherein, compounds 1 and 5 to 8 are known as alkaloid derivatives, and compounds 2 to 4 are novel alkaloid-derived compounds that were isolated for the first time.

Compound 1 is (5S)-acetyl-1-benzylpyrrolidine-2-ketone (macapyrrolidone A), compound 2 is (5S)-acetyl-1-(m-methoxybenzyl)-pyrrolidine-2-ketone (macapyrrolidone B), compound 3 is 5-methoxymethyl-1-(m-methoxybenzyl)-2-aldehyde pyrrole (macapyrroline D), compound 4 is 5-hydroxymethyl-1-(m-methoxybenzyl)-2-aldehyde pyrrole, compound 5 is 5-methoxymethyl-1-(benzyl)-2-aldehyde pyrrole, compound 6 is 5-hydroxymethyl-1-(benzyl)-2-aldehyde pyrrole, compound 7 is 3-(benzyl)-1-(hydroxy)-4-aldehyde pyridine, and compound 8 is 3-hydroxy-1-cyanomethylbenzene. Hereinafter, for convenience of description, the compounds are referred to as compounds 1 to 8, respectively.

After the biological activity test, the part of the maca extract extracted with a polar solvent (that is, parts of the second aqueous layer and the n-butanol layer) was found to have an anti-thrombotic activity, in which the part extracted with a medium-low polarity solvent (that is, the part of the methanol layer) has anti-neutrophil inflammatory and anti-allergic activities, and the part extracted with a low-polarity solvent (that is, the n-hexane layer part) has an anti-neutrophil inflammatory activity as well as a pro-angiogenic activity.

Hereinafter, the technical features of the present invention will be described in detail with accompanying drawings according to specific embodiments in order for those of ordinary skill in the art to easily understand the objects, technical features, and effects of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Hereinafter, the present invention will be described in detail with reference to the drawings.

DETAILED DESCRIPTION OF THE INVENTION

Hereinafter, the technical features of the present invention will be described with reference to the drawings according to specific embodiments. Those having ordinary skill in the art may easily understand other advantages and effects of the present invention from the features disclosed herein. Further, the present invention may be implemented or applied by other different specific embodiments. Each detail herein may be subject to various aspects and applications, and other various embodiments are applicable within the scope without departing from the spirit of the present invention.

Unless otherwise defined, all terms (including technical and scientific terms) used herein may have the same meaning as commonly understood by those having ordinary skill in the art.

It is also noted that the terms such as commonly used dictionary definitions will be interpreted to have definitions consistent with meanings in the context of the relevant art and the present invention, and will not to be interpreted in an idealized or overly formal sense, unless explicitly defined herein.

Materials

A voucher specimen (No. *Lepidium*-1) of dried tuber section plant material from maca (*Lepidium meyenii* Walp.) is stored at the Graduate Institute of Natural Products in Kaohsiung Medical University, Kaohsiung City, Taiwan.

Example 1

Method for Extraction and Separation.

Figure 1:
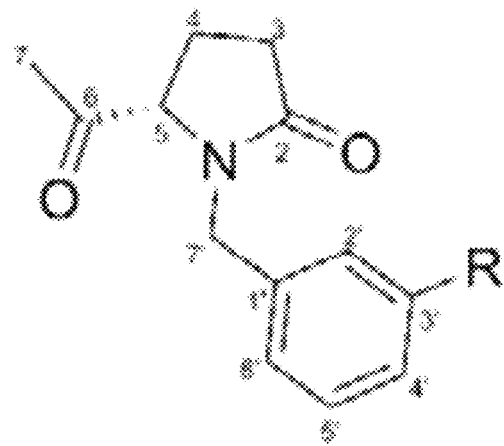
FIG. 1 is a diagram schematically showing a compound structure of a maca extract alkaloid derivative extracted according to the present invention.
Figure 1:
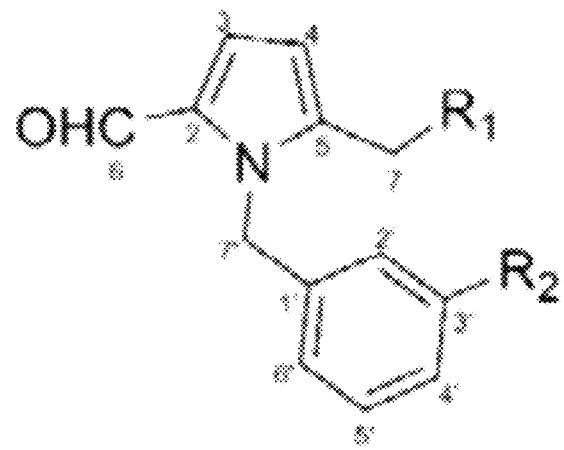
Figure 1:
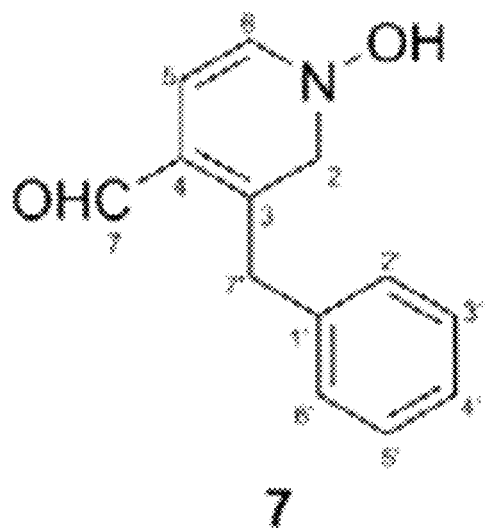
Figure 1:
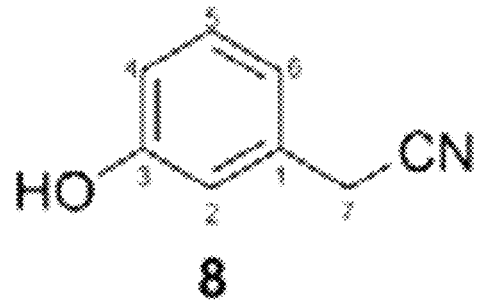
Figure 2:
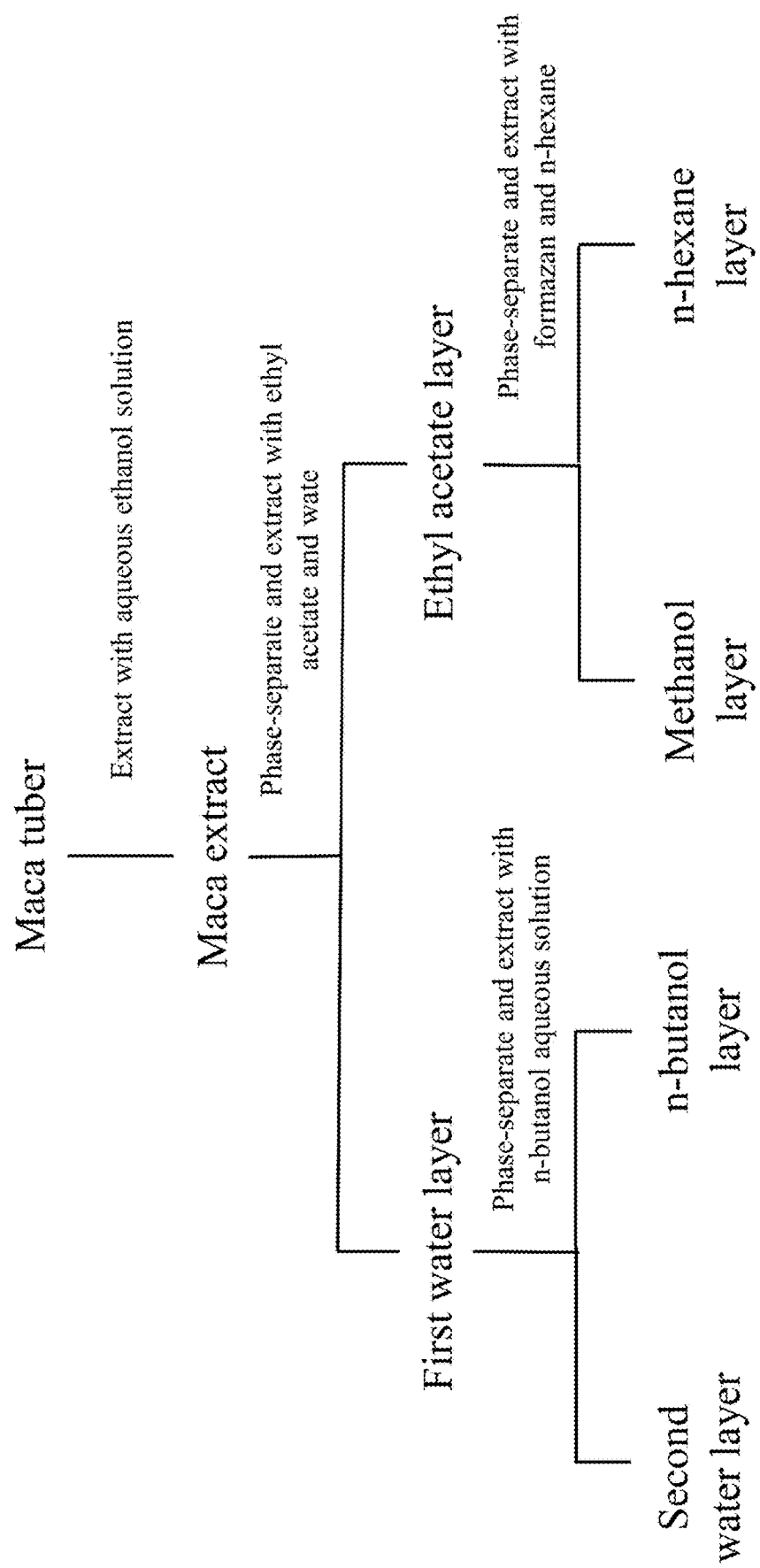
FIG. 2 is a flowchart schematically showing the maca liquid extraction of the present invention.

FIG. 2 is a flowchart schematically showing the maca liquid extraction of the present invention. Dried tuber slices (1.5 kg) of maca were extracted with 95% ethanol aqueous solution at room temperature, in which 4 L of ethanol aqueous solution were used every time for the extraction conducted 4 times consecutively, and then the combined extracts were concentrated under reduced pressure, thereby obtaining a maca crude extract (400.3 g). The maca crude extract was phase-separated and extracted with ethyl acetate and water (the volume ratio of 1:1), thereby obtaining a first aqueous layer extract (370.1 g) and an ethyl acetate layer extract (27.7 g); the first aqueous layer was phase-separated and extracted with n-butanol (the volume ratio of 1:1), thereby obtaining a second aqueous layer extract (351.6 g) and an n-butanol layer extract (15.0 g); and the ethyl acetate layer extract was phase-separated and extracted with 75% aqueous methanol solution and n-hexane (the volume ratio of 1:1), thereby obtaining a methanol layer extract (6.7 g) and an n-hexane layer extract (3.32 g).

The n-hexane layer extract was eluted with Sephadex LH-20 open column chromatography (150 cm×4.0 cm i.d.), in which the eluents were dichloromethane/methanol (the volume ratio of 1:1), so that the alkanoidamides (or macamides)-enriched fraction was obtained after elution.

Figure 3:
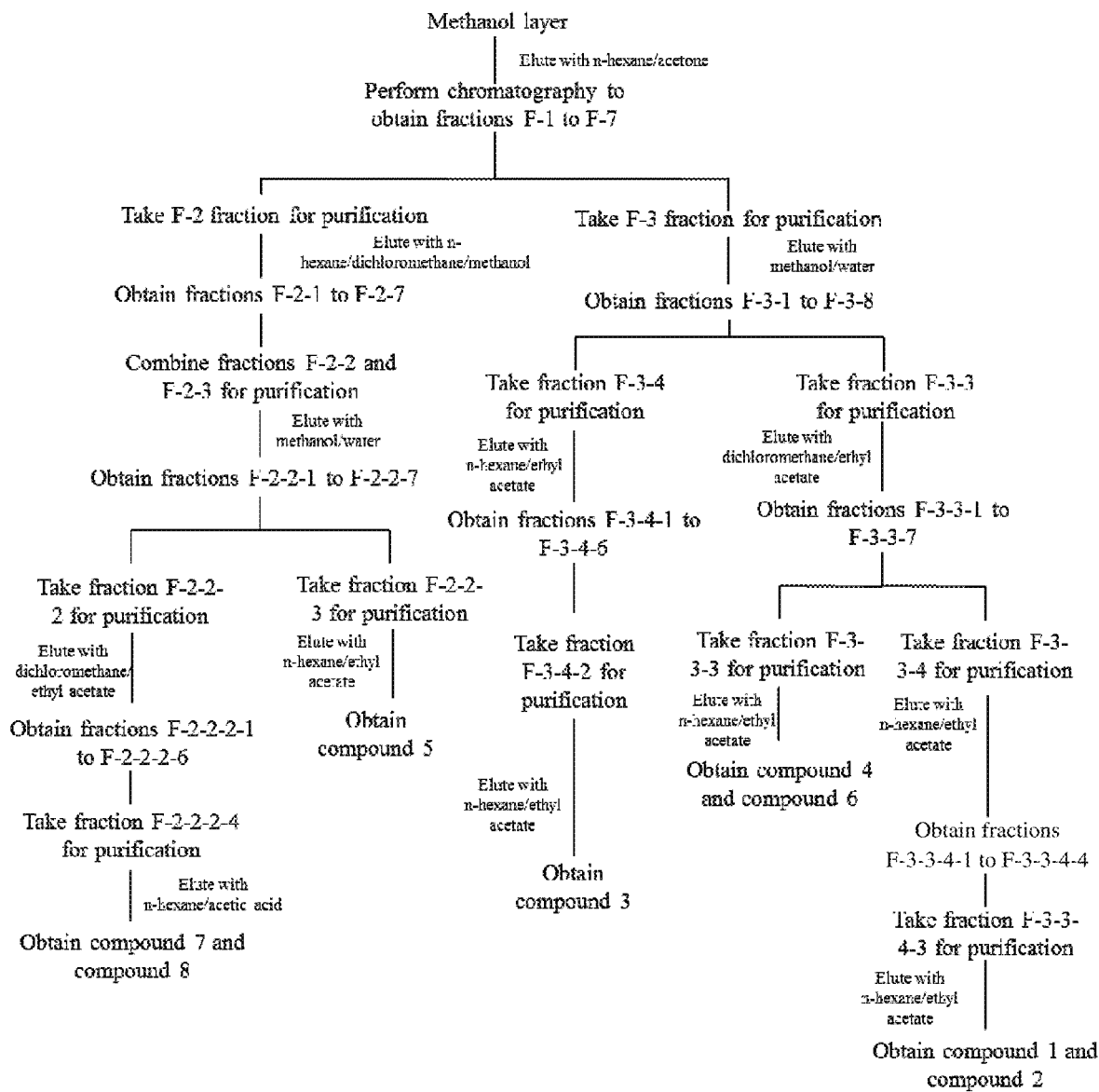
FIG. 3 is a flowchart schematically showing that column chromatography is performed on a methanol layer after liquid-phase extraction of maca according to the present invention.

FIG. 3 is a flowchart schematically showing that column chromatography is performed on a methanol layer after liquid-phase extraction of maca according to the present invention. The methanol layer extract was eluted with a silica gel chromatography column (30 cm×5.5 cm i.d.), in which the eluents were n-hexane/acetone (500 mL total), the elution were performed by the two eluents in the volume ratio of 4:1, 3:1, 2:1, 1:1 and 0:1 (that is, the acetone only) sequentially, fractions were subsequently collected and combined, and the combined fractions were divided into 7 main fractions F-1 to F-7 by chromatography. Fraction F-2 (461.01 mg) was eluted with a silica gel chromatography column (30 cm×3.0 cm i.d.), and the eluents were n-hexane/dichloromethane/methanol (200 mL total), in which the elution was performed by these three eluents in the volume ratio of 50:10:0, 40:10:1, 20:10:1, 10:10:1, 5:10:1 and 0:10:1 sequentially, thereby obtaining 7 fractions F-2-1 to F-2-7; Fraction F-2-2 (348.40 mg) and fraction F-2-3 (65.84 mg) were combined and eluted using an octa decyl silane (ODS, that is, carbon 18) chromatography column (6.5 cm×4.0 cm i.d.), and the eluents were methanol/water (total 160 mL), that is, an aqueous methanol solution, in which the elution was performed in the volume ratio of 10%, 30%, 50%, 60%, 70%, 80%, 90%, and 100% sequentially, thereby obtaining 7 fractions F-2-2-1 to F-2-2-7; Fraction F-2-2-2 (115.50 mg) was eluted with a silica gel chromatography column (20 cm×2.5 cm i.d.), and the eluents were dichloromethane/ethyl acetate (100 mL total), in which the elution was performed by these two eluents in the volume ratio of 20:1, 10:1, 5:1, 1:1 and 0:1 sequentially, thereby obtaining 6 fractions F-2-2-2-2-1 to F-2-2-2-6; Fraction F-2-2-2-4 (58.14 mg) was eluted with a silica gel chromatography column (14 cm×2.5 cm i.d.), and the eluents were n-hexane/ethyl acetate (80 mL total), in which the elution was performed by these two eluents in the volume ratio of is 5:1, 3:1, 1:1 and 0:1 sequentially thereby, obtaining compound 7 (23.62 mg) and compound 8 (8.44 mg); and Fraction F-2-3 (23.95 mg) was applied with a Luna silica gel chromatography column (n-hexane/ethyl acetate in the volume ratio of 3:1 and at the flow rate of 2 mL/min), and separated through high performance liquid chromatography (HPLC), thereby obtaining compound 5 (6.41 mg).

In addition, fraction F-3 (728.16 mg) was eluted with an ODS chromatography column (6.5 cm×4.0 cm i.d.), the eluents were methanol/water (200 mL total), that is, an aqueous methanol solution, in which the elution was performed in the volume ratio of 10%, 30%, 50%, 60%, 70%, 75%, 80%, 85%, 90%, 95% and 100% sequentially, thereby obtaining 8 fractions F-3-1 to F-3-8; Fraction F-3-3 (203.68 mg) was eluted with a silica gel chromatography column (20 cm×2.5 cm i.d.), and the eluents were dichloromethane/ethyl acetate (100 mL total), in which the elution was performed by these two eluents in the volume ratios of 9:1, 4:1, 2:1, 1:1 and 0:1 sequentially, thereby obtaining 7 fractions F-3-3-1 to F-3-3-7; Fraction F-3-3-3 (8.86 mg) was applied with a Luna silica gel chromatography column (n-hexane/ethyl acetate in the volume ratio of 3:2 and at the flow rate of 2 mL/min), and separated through high performance liquid chromatography (HPLC), thereby obtaining compound 4 (2.04 mg); Fraction F-3-3-4 (94.00 mg) was eluted with a silica gel chromatography column (18 cm×2.5 cm i.d.), and the eluents were n-hexane/ethyl acetate (100 mL total), in which the elution was performed by these two eluents in the volume ratio of is 3:1, 2:1, 1:1 and 0:1 sequentially thereby, obtaining 4 fractions F-3-3-4-1 to F-3-3-4-4;

Fraction F-3-3-4-3 (51.53 mg) was applied with a CN chromatography column (n-hexane/ethyl acetate in the volume ratio of 1:1 and at the flow rate of 2 mL/min), and separated through high performance liquid chromatography (HPLC), thereby obtaining compound 1 (9.10 mg) and compound 2 (0.78 mg); Fraction F-3-4 (94.45 mg) was eluted with a silica gel chromatography column (20 cm×2.5 cm i.d.), and the eluents were n-hexane/ethyl acetate (100 mL total), in which the elution was performed by these two eluents in the volume ratio of is 5:1, 3:1, 1:1 and 0:1 sequentially thereby, obtaining 6 fractions F-3-4-1 to F-3-4-6; and Fraction F-3-4-2 (1.66 mg) was applied with a Luna silica gel chromatography column (n-hexane/ethyl acetate in the volume ratio of 3:1 and at the flow rate of 2 mL/min), and separated through high performance liquid chromatography (HPLC), thereby obtaining compound 3 (0.42 mg).

Example 2

Pro-Angiogenic Test

Endothelial cell culture: Isolation and culture of human CD34-positive endothelial progenitor cells (EPC) were performed using conventional methods (Chen et al., 2018); human umbilical vein endothelial cells (HUVECs) were purchased from Promo Cell (Heidelberg, Germany); and EPCs and HUVECs were maintained in MV2 medium according to a known protocol (Chung et al., 2013).

Measurement of cell growth: EPCs and HUVECs were cultured overnight at a density of $5 \times 10^3$ cells per well in a 96-well plate, and then, in the presence of the test specimen (that is, maca extract), the original medium was replaced with MV2 minimal medium and incubated for 48 hours. The measurements on EPC cell growth were as described in Yang et al., 2019.

Measurement of capillary-like tube formation: EPCs were seeded in a Matrigel-coated 96-well plate at a density of $1.25 \times 10^4$ cells per well, and incubated for 24 hours in MV2 minimal medium and test fractions, and, EPC differentiation and capillary-like formation were checked according to the scheme described in Yang et al., 2019.

The test was performed at 10 μg/mL of each liquid layer, 5 μg/mL of macamide-enriched fraction (that is, eluted n-hexane layer) and 50 μM of each isolated compound, after culture for each cell. The results are shown in Table 1 as below, in which corresponding results are indicated as mean±SEM (the test was repeated 3 times as a whole), wherein, compared to the control group (DSMO), * denotes $p<0.05$,  denotes $p<0.01$, * denotes $p<0.001$; and - denotes being untested.

TABLE 1

| Specimen | Angiogenesis test Cell growth rate (%) | |
|---|---|---|
| | EPC | HUVEC |
| Crude maca extract | — | — |
| n-hexane layer | 120 ± 1*** | 133 ± 6*** |
| Methanol layer | 99 ± 1 | 106 ± 2 |
| n-butanol layer | 107 ± 1 | 119 ± 4* |
| Second water layer | 110 ± 2* | 114 ± 2* |
| Macamide-enriched fraction | 128 ± 6*** | — |
| Compound 1 | 99 ± 1 | — |
| Compound 2 | — | — |
| Compound 3 | — | — |
| Compound 4 | 103 ± 1 | — |
| Compound 5 | 99 ± 5 | — |
| Compound 6 | 104 ± 4 | — |

TABLE 1-continued

| Specimen | Angiogenesis test Cell growth rate (%) | |
|---|---|---|
| | EPC | HUVEC |
| Compound 7 | 105 ± 3 | — |
| Compound 8 | 103 ± 2 | — |
| VEGF (20 ng/mL) | 128 ± 2*** | 122 ± 2*** |

It can be seen that the vascular endothelial growth factor (VEGF) is an important mediator of angiogenesis serving as a positive control, and the n-hexane layer extract significantly increased the cell growth of EPC and HUVEC based on Table 1. In addition, the maca amide-enriched fraction derived from the n-hexane layer further increased the cell growth rate to 128±6%. In order to evaluate the angiogenic activity of the maca extract, the n-hexane layer and the macamide-enriched fraction were further compared.

Figure 4:
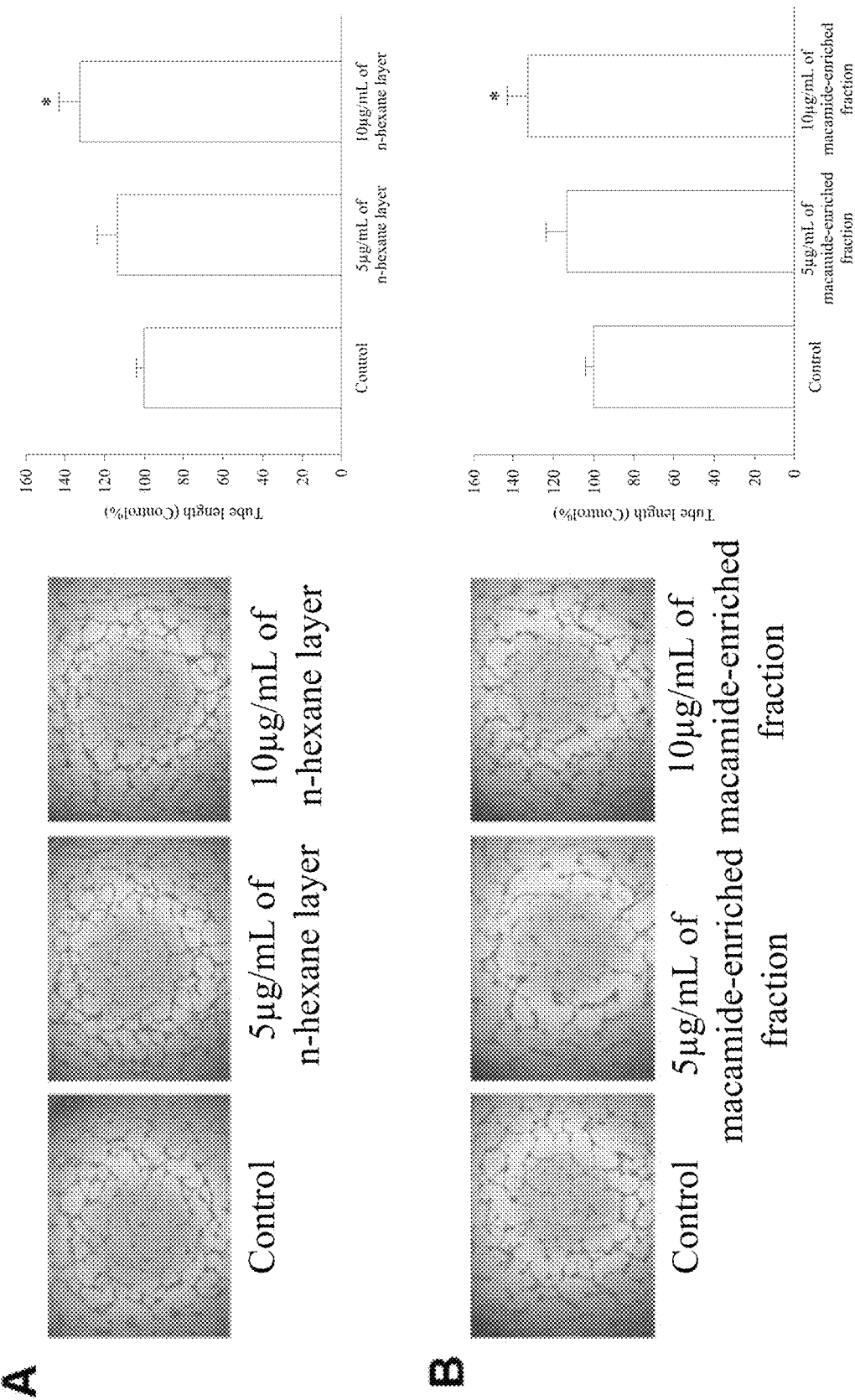
FIG. 4 depicts the effect of n-hexane layer and macamide-enriched fraction on tube formation in human endothelial progenitor cells, in which A in FIG. 4 shows the n-hexane layer, and B in FIG. 4 show the macamide-enriched fraction.

FIG. 4 depicts the effect of n-hexane layer and macamide-enriched fraction on tube formation in human endothelial progenitor cells, in which A in FIG. 4 shows the n-hexane layer, and B in FIG. 4 show the macamide-enriched fraction. As shown in the drawings, both of the n-hexane layer and the macamide-enriched fraction are dependent on concentration. In other words, as the concentration was increased, the capillary formation length of EPC was increased. Accordingly, it can be seen from the test results that both of the n-hexane layer extract and the macamide-enriched fraction thereof have pro-angiogenic activity so as to improve tissue anemia and vascular regeneration.

Example 3

Anti-Thrombotic Test

Measurement on in-vitro thrombus formation: The measurement on in-vitro thrombus formation was conducted using the scheme described in Kao et al., 2021.

Human whole blood loaded with fluorescent dye $DiOC_{6(3)}$ passed through a collagen layer flow chamber (μ-SlideVI0.1) with perfusion at a wall shear rate of $1500 \text{ s}^{-1}$ for 2 minutes followed by washing with phosphate buffer, three random visual fields per chamber were recorded using a CCD camera, and a thrombus-covered area was analyzed using Image J software.

The 50 μg/mL concentration of the crude maca extract and each liquid-extracted fraction (that is, the n-hexane layer, second aqueous layer, methanol layer, and n-butanol layer) were whole blood treated, thereby measuring the thrombus formation under whole blood flow conditions, wherein the methanol layer and the n-hexanol layer were not tested, because high concentrations may cause platelet aggregation. The results are shown in Table 2 below, and the corresponding results are indicated as mean±SEM (the test was repeated 3 times as a whole), in which * denotes $p<0.05$,  denotes $p<0.01$, * denotes $p<0.001$; and N/A denotes that the specimen forms mycelium added to the medium, and accordingly, the results cannot be proven.

TABLE 2

| Specimen | Anti-thrombotic test Inhibition rate (%) |
|---|---|
| Crude maca extract | 27.8 ± 4.2 |
| n-hexane layer | N/A |
| Methanol layer | N/A |
| n-butanol layer | 59.9 ± 6.1** |
| Second water layer | 50.5 ± 12.1** |

As shown in Table 2, the whole blood specimen treated with the crude maca extract had the thrombus area decreased by 27.8±4.2%, and the n-butanol layer and the second aqueous layer exhibited better anti-thrombotic activities, in which the thrombus areas were decreased by 59.9±6.1% and 50.5±12.1%, respectively. Accordingly, the test results shows that the maca fraction extracted with a polar solvent has anti-thrombotic activity.

Example 4

Anti-Neutrophil Inflammation Test

Isolation of human neutrophil: According to the standard scheme of dextrin sedimentation, neutrophils was obtained from peripheral blood, and then, the neutrophils were purified by centrifugation and erythrocyte hypotonic degradation in a Ficoll-Hypaque gradient; and then, it was confirmed by the trypan blue exclusion test that the purified neutrophils contained more than 98% live cells, and the purified neutrophils were suspended in HBSS without calcium at 4° C. (Yang et al., 2013) prior to the test.

Measurement on superoxide anion generation and measurement on elastase release inhibition:

The level of superoxide anion generation by neutrophil activation was measured and determined based on the ferrocytochrome c reduction method according to Yang et al., 2013. In other words, human neutrophil cells ($6\times10^5$ cells/mL) were mixed with 0.6 mg/mL of ferrocytochrome c and 1 mmol/L of CaCl at 37° C., and then the cells were treated with the test specimens having different concentrations (that is, maca extract) or DMSO (0.1% as control) for 5 minutes; thereafter, 10 minutes before activation with 100 nM of fMLF, the cells were incubated with cytochalasin B (1 µg/mL) for 3 minutes, changes in absorbance according to the decrease in ferrocytochrome c at a wavelength of 500 nm with continuous stirring were continuously monitored using a spectrophotometer, and reactions were calculated with and without superoxide dismutase (SOD, 100 U/mL) with dividing by the extinction coefficient of the decreased ferrocytochrome c ($21.1 \text{ mM}^{-1} \text{ cm}^{-1}$) reduction, thereby obtaining the difference value.

The elastase release was used to measure degranulation of azurophilic granules in activated neutrophils (Yang et al., 2013); and the measurement was performed using methoxysuccinyl-Ala-Ala-Pro-Val-p-nitroaniline as an elastase matrix. At 37° C., neutrophils ($6\times10^5$ cells/mL) were added to a mixture of matrix (100 µmol/L) and $CaCl_2$ (1 mmol/L), and treated with the test specimens having different concentrations (that is, maca extract) or DMSO (0.1% as control) for 5 minutes, and then the cells were stimulated by using fMLF (100 nM)/CB (0.5 µg/mL), and changes in absorbance at the 405 nm wavelength were continuously monitored to measure the release of elastase, in which genistein and LY294002 were used as positive controls. The test results are shown in Table 3 below. The corresponding results are indicated as mean±SEM (the test was repeated 3 or 4 times), in which * denotes p<0.05,  denotes p<0.01, * denotes p<0.001; and - denotes being untested.

TABLE 3

| | Anti-neutrophil inflammation test Inhibition rate (%) | |
| --- | --- | --- |
| Specimen | Superoxide anion generation | Elastase release |
| crude maca extract | — | — |
| n-hexane layer | 81.46 ± 5.56*** | 96.39 ± 5.89*** |
| Methanol layer | 101.12 ± 0.26*** | 110.88 ± 0.24*** |

TABLE 3-continued

| | Anti-neutrophil inflammation test Inhibition rate (%) | |
| --- | --- | --- |
| Specimen | Superoxide anion generation | Elastase release |
| n-butanol layer | 75.96 ± 2.89*** | 27.86 ± 1.54*** |
| Second water layer | 3.07 ± 6.75 | 5.54 ± 0.72** |
| Macamide-enriched fraction | — | — |
| Compound 1 | 7.50 ± 1.96* | 1.59 ± 0.99 |
| Compound 2 | — | — |
| Compound 3 | — | — |
| Compound 4 | 1.05 ± 0.78 | 0.00 ± 0.59 |
| Compound 5 | 21.59 ± 5.35* | 3.33 ± 0.50** |
| Compound 6 | 5.44 ± 2.18 | 2.69 ± 0.49** |
| Compound 7 | 10.94 ± 1.84** | 2.48 ± 3.05 |
| Compound 8 | 0.45 ± 4.35 | 1.78 ± 2.29 |
| Genistein (10 µM) | 93.37 ± 0.93*** | 44.22 ± 3.72*** |
| LY294002 (10 µM) | 95.31 ± 2.78*** | 72.80 ± 4.03*** |

As shown in Table 3, it can be seen that both anti-neutrophil inflammatory activities of the methanol layer and the n-hexane layer were highly significant, wherein the fMLF-activated neutrophil function was completely eliminated (101.12±0.26% and 110.88±0.24%, respectively), and the methanol layer (10 µg/mL) exhibited the strongest inhibitory action on superoxide anion generation and elastase release among all liquid extraction layers; in addition, the n-hexane layer (10 µg/mL) exhibited an effective inhibitory action on superoxide anion generation (81.46±5.56%) and elastase release (96.39±5.89%), and the n-butanol layer exhibited a significant inhibitory action only on superoxide anion generation (75.96±2.89%).

In the above test, only compound 5 (10 µM) had a slight inhibitory action on fMLF/CB-induced neutrophil superoxide anion generation (21.59±5.35%); and all of the isolated compounds did not exhibit significant action on the anti-neutrophil inflammatory activity compared with the results of the methanol layer and the n-hexane layer.

Accordingly, based on the above test results, it was found that the part extracted with the medium-low polarity solvent and the part extracted with the low-polarity solvent from maca had anti-neutrophil inflammatory activity.

Example 5

Anti-Allergy Test

Cell culture: Mucosal mast cell-induced murine basophil leukemia (RBL-2H3) was cultured using the method according to Korinek et al., 2017. Cells were cultured using DMEM medium supplemented with 10% FBS, and additional 100 U/mL penicillin and 100 µg/mL streptomycin. The cells were cultured in 10 cm Petri dishes in a 5% $CO_2$ incubator at 37° C., the cells were secondary cultured in 80% confluent trypsin, and then seeded on culture plates at a density of $2\times10^5$ cells/mL for secretion measurement.

Measurement on cell viability: RBL-2H3 cells were seeded in a 96-well plate at a concentration of $2\times10^4$ cells/well overnight, specimens having different concentrations (that is, maca extract, dissolved in DMSO) or untreated controls (1% DMSO in Tyrode buffer; 135 mM NaCl, 5 mM KCl, 1.8 mM CaCl, 1.0 mM $MgCl_2$, 5.6 mM glucose, 20 mM HEPES and 1 mg/ml BSA, pH 7.4) were used to treat the cells, the media was removed from the wells after incubation at 37° C., 5% CO2, and an MTT solution (5 mg/mL) stock solution was diluted 1:10 in the medium and then added to the wells (100 μL per well); Thereafter, the cells were incubated at 37° C., 5% CO for 1 hours, the medium was removed, the formed Formazan crystals (which can be formed only in normal healthy cells) were dissolved in 100 μL DMSO, and the absorbance at 574 nm wavelength was measured using a microplate reader in which the plates were gently shaked before the measurement. Cell viability values for the specimens were calculated and indicated as a percentage (%) of the control groups (untreated cells).

Measurement on inhibition of β-hexosaminidase release in A23187 and antigen-induced RBL-2H3 cells: RBL-2H3 cells were distributed in a 96-well plate at a density of $2 \times 10^4$ cells/well, the cells in the antigen induction test were seeded to a 48-well plate at a density of $3 \times 104$ cells/well, sensitized with anti-DNPIgE (0.05 μg/ml), and then incubated overnight at 37° C., 5% CO2, so that the cells were allowed to fully adhere to the bottom of the wells; thereafter, specimens having different concentrations (that is, maca extract dissolved in DMSO) or Tyrode buffer (1% DMSO as untreated control) were added to each well (100 μL) and incubated at 37° C., 5% CO2 for 30 minutes; and subsequently, the supernatant was removed and the cells were stimulated with calcium ionophore A23187 (0.5 μM, measured for A23187 induction) or a cross-linked antigen DNP-BSA (100 ng/ml, measured for antigen induction), incubated at 37° C., 5% CO2 for 30 minutes, and unstimulated cells were degraded with 0.5% TritonX-100 solution to release β-hexosaminidase, or untreated to spontaneously release β-hexosaminidase. Equivalently divided supernatants (50 μL) of control wells and experimental wells were incubated with an equal volume (50 μL) of 1 μM p-NAG prepared in 0.1 M citrate buffer (pH 4.5), in which the buffer is formed as a matrix of released β-hexosaminidase; the reaction, after 1 hour incubation at 37° C., was stopped by adding 100 μL of termination buffer (0.1M Na2/NaHCO3, pH 10.0), and then, the absorbance at a wavelength of 405 nm was measured with a microplate reader. The percentage of inhibiting RBL-2H3 cells from releasing β-hexosaminidase was calculated as the percentage of control (untreated stimulated cells), and azelastine (20 μM) was used as a positive control. The test results are shown in Tables 4 to 6 below, and the corresponding results are indicated as mean±SEM (the test was repeated 3 times), wherein * denotes $p<0.05$,  denotes $p<0.01$, * denotes $p<0.001$; - denotes being untested; and N/A denotes that the specimen forms mycelium added to the medium, and accordingly, the results cannot be proven.

TABLE 4

| | Anti-allergy test | | | |
|---|---|---|---|---|
| | A23187-induced β-hexosaminidase release | | Antigen-induced β-hexosaminidase release | |
| Specimen | Inhibition rate (%) | $IC_{50}$ | Inhibition rate (%) | $IC_{50}$ |
| Crude maca extract | 14.7 ± 2.7*** | >200 | 6.7 ± 3.6 | >200 |
| n-hexane layer | N/A | N/A | N/A | N/A |
| Methanol layer | 83.0 ± 2.2*** | 97.1 | 75.0 ± 5.1*** | 102.7 |
| n-butanol layer | 22.3 ± 2.6*** | >200 | 28.7 ± 2.9*** | >200 |
| Second water layer | 4.3 ± 2.4 | >200 | 0.7 ± 0.5 | >200 |
| Macamide-enriched fraction | — | — | — | — |
| Compound 1 | 4.0 ± 1.7 | >200 | 9.0 ± 3.7 | >200 |
| Compound 2 | — | — | — | — |
| Compound 3 | 4.7 ± 0.7 | >200 | 10.7 ± 3.3 | >200 |
| Compound 4 | 6.7 ± 1.4 | >200 | 10.0 ± 4.1 | >200 |
| Compound 5 | 51.3 ± 4.6*** | 96.1 | 11.7 ± 5.9 | >200 |
| Compound 6 | 9.7 ± 2.2 | >200 | 3.7 ± 3.0 | >200 |
| Compound 7 | 6.0 ± 0.8 | >200 | 8.0 ± 1.2 | >200 |
| Compound 8 | 8.3 ± 3.4 | >200 | 13.0 ± 2.6 | >200 |
| Azelastine | 47.7 ± 3.2*** | — | 54.3 ± 1.8*** | — |

TABLE 5

| Specimen | Viability of RBL-2H3 cells at 200 μg/ml | Percentage of inhibiting A23187-induced β-hexosaminidase release (%) | | | | Percentage of inhibiting antigen-induced β-hexosaminidase release (%) | | | |
|---|---|---|---|---|---|---|---|---|---|
| | | 20 μg/mL | 100 μg/mL | 200 μg/mL | $IC_{50}$ (μg/ml) | 20 μg/mL | 100 μg/mL | 200 μg/mL | $IC_{50}$ (μg/ml) |
| Crude maca extract | 90.7% | 5.3 ± 2.4% | — | 14.7 ± 2.7%*** | — | 1.7 ± 1.0% | — | 6.7 ± 3.6% | — |
| n-hexane layer (100 μg/mL) | 92.3% | 17.0 ± 1.2%*** | 31.7 ± 2.3%*** | — | — | 9.3 ± 5.0% | 33.3 ± 6.4%*** | — | — |
| Methanol layer | 92.3% | 23.3 ± 1.0%*** | 51.0 ± 3.3%*** | 83.0 ± 2.2%*** | — | 23.3 ± 3.9%*** | 49.3 ± 5.7%*** | 75.0 ± 5.1%*** | 102.7 |
| n-butanol layer | 92.7% | 4.0 ± 1.9% | — | 22.3 ± 2.6%*** | 97.1 | 7.3 ± 2.7% | — | 28.7 ± 2.9%*** | — |
| Second water layer | 92.3% | 6.3 ± 1.9% | — | 4.3 ± 2.4% | — | 8.3 ± 1.7% | — | 0.7 ± 0.5% | — |
| Azelastine (20 μM) | 88.0% | 47.7 ± 3.2%*** | — | — | — | 54.3 ± 1.8%*** | — | — | — |

TABLE 6

| Specimen | Viability of RBL-2H3 cells at 200 µg/ml | Percentage of inhibiting A23187-induced β-hexosaminidase release (%) | | | | Percentage of inhibiting antigen-induced β-hexosaminidase release (%) | | | |
|---|---|---|---|---|---|---|---|---|---|
| | | 10 µM/mL | 100 µM/mL | 500 µM/mL | $IC_{50}$ (µM) | 10 µM/mL | 100 µM/mL | 500 µM/mL | $IC_{50}$ (µM) |
| Compound 1 | 95.3% | 2.7 ± 1.2% | 4.0 ± 1.7% | 38.0 ± 3.4%*** | — | 3.7 ± 1.9% | 5.7 ± 2.2% | 9.0 ± 3.7% | — |
| Compound 3 | 95.0% | 3.7 ± 1.5% | 4.7 ± 0.7% | 12.7 ± 0.7%** | — | 13.7 ± 1.9% | 10.7 ± 3.3% | 5.0 ± 4.1% | — |
| Compound 4 | 96.0% | 8.3 ± 1.0% | 6.7 ± 1.4% | — | — | 16.7 ± 6.6%* | 10.0 ± 4.1% | — | — |
| Compound 5 | 94.0% | 21.3 ± 3.3%*** | 51.3 ± 4.6%*** | 57.7 ± 4.3%*** | 96.1 | 9.0 ± 4.8% | 11.7 ± 5.9% | 8.3 ± 3.5% | — |
| Compound 6 | 100.0% | 5.7 ± 1.0% | 9.7 ± 2.2% | 26.0 ± 2.4%*** | 10.3 ± 3.9% | 3.7 ± 3.0% | 0.3 ± 0.3% | — | |
| Compound 7 | 94.7% | 2.0 ± 1.6% | 6.0 ± 0.8% | 18.0 ± 3.4%*** | 11.7 ± 2.6% | 8.0 ± 1.2% | 0.0 ± 0.0% | | |
| Compound 8 | 97.7% | 11.0 ± 0.8%* | 8.3 ± 3.4% | 11.7 ± 1.5%* | 13.7 ± 3.9% | 13.0 ± 2.6% | 4.0 ± 3.3% | — | |
| Azelastine (20 µM) | 88.0% | 47.7 ± 3.2%*** | — | — | — | 54.3 ± 1.8%*** | — | — | — |

As shown in Table 4, the methanol layer had a significant effect in the anti-allergy test, the release of β-hexosaminidase was inhibited from RBL-2H3 cells induced with A23187 ($IC_{50}$ 97.1 µg/mL) and antigen ($IC_{50}$ 102.7 µg/mL).

As shown in Table 5, the methylthiazolyltetrazole (MTT) assay exhibited >90% activity, the anti-allergic activities of compounds was evaluated by inhibiting the release of β-hexosaminidase in A23187 and antigen-induced RBL-2H3 cell degranulation, and the inhibition effect of the methanol layer was still significant.

As shown in FIG. 4 and Table 6, compound 5 ($IC_{50}$ 96.1 µM) exhibited the strongest inhibition effect on degranulation of A23187-induced RBL-2H3 cells, and the β-hexosaminidase release inhibition activity of compound 5 was increased in a dose-dependent manner between 10 µM and 500 µM; in addition, compound 1 (500 µM) exhibited slight inhibition (38.0±3.4%) to A23187-induced β-hexosaminidase release activity.

However, none of the compounds exhibited significant inhibition effect in the antigen-induced β-hexosaminidase release test. Thus, these results indicate that compound 5 acts through an IgE-independent allergy group, particularly, relates to inhibition of calcium influx in mast cells.

Therefore, based on the above test results, it can be seen that the part extracted with the medium-low polarity solvent from maca had anti-neutrophil inflammatory activity.

To summarize the test results obtained from the above examples, the part of maca extract extracted with a polar solvent has antithrombotic activity, in which the part extracted with a medium-low polarity solvent anti-neutrophil inflammatory and anti-allergic activities, and the part extracted with a low-polarity solvent has an anti-neutrophil inflammatory activity as well as a pro-angiogenic activity. In addition, during extracting maca, three novel alkaloid-derived compounds were also isolated for the first time.

Those having ordinary skill in the art will understand, from the aforementioned descriptions, that the present invention may be exemplified in other specific forms without departing from the disclosed technical idea or essential features. Therefore, the exemplary aspects disclosed herein are for illustrative purposes only and will not be construed as limiting the scope of the present disclosure. Whereas, the present disclosure may encompass various changes, modifications, equivalents, and other aspects that may be included within the spirit and scope of the present disclosure as defined by the following appended claims, as well as the above exemplary aspects.

What is claimed is:

1. A method of preparing a maca extract, comprising the following steps:
    extracting maca tubers with 95% ethanol aqueous solution at room temperature to obtain a crude maca extract;
    phase-separating and extracting the crude maca extract by using ethyl acetate and water, thereby obtaining a first aqueous layer extract and an ethyl acetate layer extract;
    phase-separating and extracting the ethyl acetate layer extract with 75% aqueous methanol solution and n-hexane, thereby obtaining a methanol layer extract and an n-hexane layer extract; and
    performing column chromatography on the methanol layer extract, thereby obtaining the maca extract.

2. The method of claim 1, wherein the extraction of the methanol layer extract performed by the column chromatography comprises:
    using n-hexane/acetone as an eluent and a silica gel chromatography column to perform elution on the methanol layer extract, and combining the eluted fractions and then dividing the combined fractions into 7 main fractions F-1 to F-7 by chromatography;
    performing elution on the fraction F-3 by an ODS chromatography column with methanol/water as an eluent, thereby obtaining 8 fractions F-3-1 to F-3-8;
    performing elution on the fraction F-3-3 by using a silica gel chromatography column with dichloromethane/ethyl acetate as an eluent, thereby obtaining 7 fractions F-3-3-1 to F-3-3-7;
    performing elution on the fraction F-3-3-3 by using a Luna chromatography column through high performance liquid chromatography with n-hexane/ethyl acetate as an eluent, thereby obtaining 5-hydroxymethyl-1-(m-methoxy obtaining benzyl)-2-aldehyde pyrrole;
    performing elution on the fraction F-3-3-4 by using a silica gel chromatography column with n-hexane/ethyl acetate as an eluent, thereby obtaining 4 fractions F-3-3-4-1 to F-3-3-4-4;
    performing elution on the fraction F-3-3-4-3 by using a CN chromatography column through high performance liquid chromatography with n-hexane/ethyl acetate as an eluent, thereby obtaining (5S)-acetyl-1-(m-methoxy obtaining benzyl)-pyrrolidin-2-ketone;

performing elution on the fraction F-3-4 by using a silica gel chromatography column with n-hexane/ethyl acetate as an eluent, thereby obtaining 6 fractions F-3-4-1 to F-3-4-6; and performing elution on the fraction F-3-4-3 by using a Luna chromatography column through high performance liquid chromatography with n-hexane/ethyl acetate as an eluent, thereby obtaining 5-methoxymethyl-1-(m-methoxybenzyl)-2-aldehyde pyrrole.

3. The method of claim 1, wherein the maca extract comprises at least one compound selected from the group consisting of:

(5S)-acetyl-1-(m-methoxybenzyl)-pyrrolidine-2-ketone;
5-methoxymethyl-1-(m-methoxybenzyl)-2-aldehydepyrrole; and
5-hydroxymethyl-1-(m-methoxybenzyl)-2-aldehydepyrrole.

* * * * *